United States Patent [19]

Aoki et al.

[11] Patent Number: 5,556,987
[45] Date of Patent: Sep. 17, 1996

[54] PROCESS FOR PRODUCING PYRAZOLECARBOXAMIDE DERIVATIVE

[75] Inventors: Mario Aoki; Akira Ogawa, both of Minami-ashigara, Japan

[73] Assignee: Fuji Photo Film Co., Ltd., Kanagawa, Japan

[21] Appl. No.: 548,266

[22] Filed: Oct. 25, 1995

[30] Foreign Application Priority Data

Nov. 10, 1994 [JP] Japan .................................. 6-276505

[51] Int. Cl.$^6$ ...................... C07D 231/20; C07D 231/22
[52] U.S. Cl. ...................... 548/369.7; 544/140; 546/211; 548/364.1
[58] Field of Search .................. 548/369.7, 364.1; 544/140

[56] References Cited

U.S. PATENT DOCUMENTS

| | | | |
|---|---|---|---|
| 4,348,528 | 9/1982 | Breda et al. | 548/369.7 |
| 4,833,246 | 5/1989 | Adachi et al. | 548/369.7 |

OTHER PUBLICATIONS

R. D. Gless, Jr., Lewis Acid Mediated Aminolysis of Esters: Conversion Of Methyl (S)–(–)–2–Chloropropionate To (S)–(+)–N,N–Diethyl–2–Chloropropionamide, 1986, Synthetic Communications, 16(6), pp. 633–638.

J. I. Levin et al., An Alternative Procedure For the Aluminum–Mediated Conversion Of Esters To Amides, Synthetic Communications, 12(13), pp. 989–993.

F. Porta et al., Reactions Of Esters With Amines Catalysed By Metal Centres, 1988, Gazzetta Chimica Italiana, 118, pp. 475–477.

*Primary Examiner*—Robert W. Ramsuer
*Attorney, Agent, or Firm*—Birch, Stewart, Kolasch & Birch, LLP

[57] ABSTRACT

A process for producing a pyrazolecarboxamide derivative represented by formula (C) which comprises reacting a pyrazolecarboxylic ester compound represented by formula (A) with an amine compound represented by formula (B) in the presence of a Lewis acid:

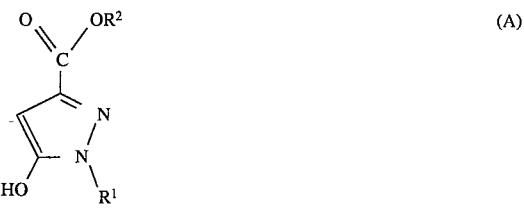

(A)

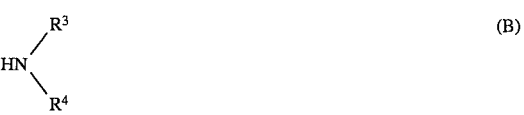

(B)

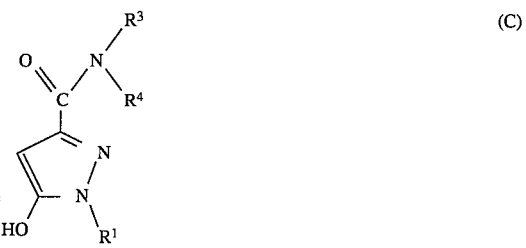

(C)

wherein $R^1$ represents a hydrogen atom, a substituted or unsubstituted alkyl group, a substituted or unsubstituted aryl group, or a substituted or unsubstituted heterocyclic group; $R^2$ represents a substituted or unsubstituted alkyl group; and $R^3$ and $R^4$ each represents a hydrogen atom, a substituted or unsubstituted alkyl group, a substituted or unsubstituted aryl group, or a substituted or unsubstituted heterocyclic group, provided that $R^3$ and $R^4$ may be bonded to each other to form a ring.

11 Claims, No Drawings

PROCESS FOR PRODUCING PYRAZOLECARBOXAMIDE DERIVATIVE

FIELD OF THE INVENTION

The present invention relates to a process for producing a pyrazolecarboxamide derivative represented by formula (C) which is useful as a dye intermediate or for producing a medicine, agricultural chemical, etc. More particularly, this invention relates to a process for producing a pyrazolecarboxamide derivative from a pyrazolecarboxylic ester compound and an amine compound using a Lewis acid as an activating agent.

BACKGROUND OF THE INVENTION

Pyrazolecarboxamide derivatives having a carbamoyl group at the 3-position are useful compounds as, e.g., a dye intermediate and a base compound for producing medicines or agricultural chemicals, and are especially useful as an intermediate for photographic dyes (see, e.g., JP-A-51-77327 and JP-A-63-139949). (The term "JP-A" as used herein means an "unexamined published Japanese patent application.")

Several processes for synthesizing pyrazolecarboxamide derivatives have conventionally been known; these processes are generally based on the aminolysis of esters (see, e.g., JP-A-63-139949). However, when a secondary amine or arylamine having reduced nucleophilicity, such as morpholine or aniline, is used, the aminolysis reaction should be conducted at a high temperature for a prolonged time period, although aminolysis with a highly nucleophilic primary alkylamine, such as ethanolamine, proceeds relatively easily. Thus, those prior art processes are unsuitable for industrial production.

On the other hand, there are also several known processes for synthesizing pyrazolecarboxamide derivatives without via ester aminolysis. Such processes, for example, include a method in which a 3-carboxylated compound is reacted with a sulfonic acid chloride derivative to yield a mixed acid anhydride and the anhydride is amidated (see JP-A-58-111641) and a method in which amidation is conducted after the 5-position hydroxyl group is protected by being converted to an ester group (see JP-A-2-193973 and JP-A-2-193974). However, the former method, in which the desired compound is obtained via a mixed acid anhydride, has a drawback that when the starting compounds have a reactive hydroxyl group in the molecule, side reactions occur in a considerable degree to result in a reduced yield. The latter method, which involves protection of a hydroxyl group, has a drawback that the necessity of additional two steps, i.e., protection and protecting-group elimination, leads to an increased cost, although a high yield is attainable.

There is a method in which a Lewis acid is used for amidating an ester by aminolysis. This method, however, is not frequently used generally, since the acidity of the Lewis acid is reduced, or the Lewis acid reacts with an amine to consume the amine. The following are examples of a limited number of such methods.

1. R. D. Gless, Jr., *Synth. Comm.*, 16, 633 (1986)

Aminolysis of a 2-chloropropionic ester

2. F. Porta, M. Pizzotti, C. Crotti and S. Cenini, *Gazz. Chem. Ital.*, 118, 475 (1988)

Aminolysis of ethyl acetate or propionate with a primary amine

3. J. I. Levin, E. Turos and S. M. Weinreb, *Synth. Comm.*, 12, 989 (1982)

Aminolysis using an alkylaluminum

However, methods 1 and 2 have a drawback that the usable substrates are limited to only a small part of aliphatic esters and amines. Method 3 has a drawback that trimethylaluminum used therein as a reagent is an ignitable water-prohibiting compound, although the method is applied to various esters. Thus, these three methods each has a drawback when used for industrial production. In particular, there has been no report on application to a compound having in the molecule a reactive hydroxyl group and a heterocyclic group capable of coordinating with a Lewis acid, such as the substrate compound used in the present invention.

The present inventors made investigations in order to develop a method for synthesizing the desired pyrazolecarboxamide derivative by aminolysis of a pyrazolecarboxylic ester. As a result, it has been found that when a Lewis acid is used as an activating agent, the aminolysis of a pyrazolecarboxylic ester with an amine compound proceeds readily to yield the desired pyrazolecarboxamide derivative. The present inventors have further found that the Lewis acid used for activation functions as a catalyst. In industrial production, this function of the Lewis acid is of great significance from the standpoints of post-treatment after reaction, withdrawal of the reaction product, and environmental conservation.

SUMMARY OF THE INVENTION

Accordingly, an object of the present invention is to provide an industrially effective process for producing in high yield a pyrazolecarboxamide derivative useful as a dye intermediate, etc.

The object of the present invention is accomplished with a process for producing a pyrazolecarboxamide derivative represented by formula (C) which comprises reacting a pyrazolecarboxylic ester compound represented by formula (A) with an amine compound represented by formula (B) in the presence of a Lewis acid:

(A)

(B)

(C)

wherein $R^1$ represents a hydrogen atom, a substituted or unsubstituted alkyl group, a substituted or unsubstituted aryl group, or a substituted or unsubstituted heterocyclic group; $R^2$ represents a substituted or unsubstituted alkyl group; and $R^3$ and $R^4$ each represents a hydrogen atom, a substituted or unsubstituted alkyl group, a substituted or unsubstituted aryl group, or a substituted or unsubstituted heterocyclic group, provided that $R^3$ and $R^4$ may be bonded to each other to form a ring.

DETAILED DESCRIPTION OF THE INVENTION

Formula (A) is explained first in detail.

$R^1$ represents a hydrogen atom, a substituted or unsubstituted alkyl group, a substituted or unsubstituted aryl group, or a substituted or unsubstituted heterocyclic group. More particularly, the alkyl group is a linear or branched alkyl group having 1 to 12 carbon atoms, and the aryl group represents a phenyl or naphthyl group having 6 to 10 carbon atoms. Further, the heterocyclic group represents a 5- to 7-membered, saturated or unsaturated heterocyclic group. These groups may have an organic substituent bonded through a carbon, oxygen, nitrogen, or sulfur atom and a substituent such as a hydroxyl group, a halogen atom, or a sulfo group. Examples of the organic substituent include alkyl groups, aryl groups, heterocyclic groups, a cyano group, acyl groups, a carboxyl group, aryloxy groups, alkoxy groups, heterocycle-oxy groups, an amino group, a sulfamoylamino group, sulfonamido groups, alkylthio groups, arylthio groups, heterocycle-thio groups, a sulfamoyl group, a sulfonyl group, and a sulfinyl group.

The substituents represented by $R^1$ are explained in more detail.

Examples of the substituted or unsubstituted alkyl group represented by $R^1$ include methyl, ethyl, propyl, isopropyl, n-butyl, s-butyl, cyclopentyl, cyclohexyl, methoxyethyl, 2-hydroxyethyl, carboxymethyl, phenoxyethyl, methanesulfonylethyl, (3-pentadecylphenoxy)propyl, 3-(2,4-diaminophenoxy)propyl, 2-sulfoethyl, 4-sulfobutyl, and 2'-sulfobenzyl.

Examples of the substituted or unsubstituted aryl group represented by $R^1$ include phenyl, 4-tolyl, 4-methoxyphenyl, 2,4-xylyl, 2-chlorophenyl, 4-carboxyphenyl, 4-sulfophenyl, 2,5-disulfophenyl, 1-naphthyl, and 1-(3,5-disulfonaphthyl).

Examples of the substituted or unsubstituted heterocyclic group represented by $R^1$ include 2-tetrahydrofuranyl, 2-tetrahydrothienyl, 1-piperidino, 2-pyridyl, 1-pyrazolyl, 2-thienyl, 2-pyrimidinyl, 2-benzothiazolyl, and 3-(1,1-dioxotetrahydrothienyl).

The substituted or unsubstituted alkyl group represented by $R^1$ is preferably a substituted or unsubstituted alkyl group having 1 to 7 carbon atoms, and is more preferably an unsubstituted methyl group or an alkyl group having 1 to 7 carbon atoms and substituted with a carboxyl, sulfo, or hydroxyl group.

The substituted or unsubstituted aryl group represented by $R^1$ is preferably a substituted or unsubstituted phenyl group, more preferably a phenyl group substituted with a carboxyl or sulfo group.

$R^1$ is preferably a hydrogen atom, an alkyl group having 1 to 7 carbon atoms optionally substituted with a carboxyl, sulfo, or hydroxyl group, a phenyl group optionally substituted with a carboxyl or sulfo group, or 3-(1,1-dioxotetrahydrothienyl). $R^1$ is particularly preferably a hydrogen atom, methyl, carboxymethyl, a sulfo-substituted linear alkyl group having 2 to 4 carbon atoms, 2'-sulfobenzyl, 4-sulfophenyl, 2,5-disulfophenyl, and 3-(1,1-dioxotetrahydrothienyl). Of these, methyl is the most preferred.

The alkyl group represented by $R^2$ is a linear or branched alkyl group having 1 to 12 carbon atoms, which may have a substituent. Preferred example of the substituent includes an alkoxy group. The alkoxy group may further have an alkoxy group.

Specific examples of the substituted or unsubstituted alkyl group represented by $R^2$ include methyl, ethyl, propyl, isopropyl, n-butyl, s-butyl, 1-(2-ethylhexyl), decyl, dodecyl, cyclopentyl, cyclohexyl, methoxyethyl, ethoxyethyl, methoxyethoxyethyl, and methoxyethoxyethoxyethyl.

$R^2$ is preferably an alkyl group having 1 to 6 carbon atoms, more preferably a linear alkyl group having 1 to 4 carbon atoms, particularly preferably methyl or ethyl.

Specific examples of the pyrazolecarboxylic ester for use in this invention are given below, but the ester should not, of course, be construed as being limited thereto.

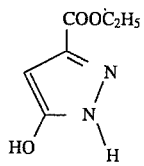

A-1

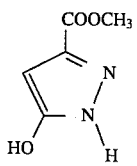

A-2

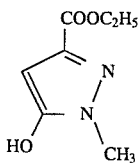

A-3

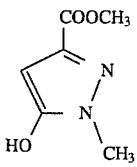

A-4

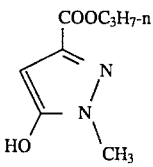

A-5

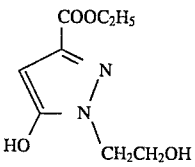

A-6

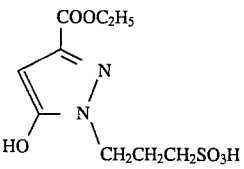

A-7

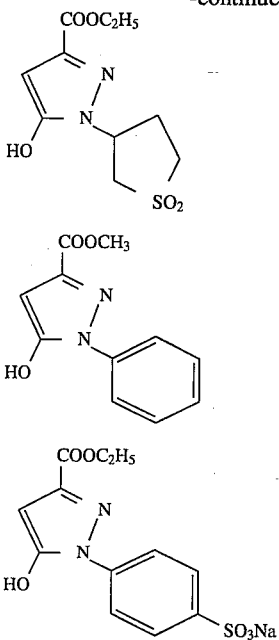

The pyrazolecarboxylic ester compound represented by formula (A) can be easily synthesized from the corresponding hydrazine compound and oxalacetic ester compound.

The amine compound represented by formula (B) is then explained in detail.

The amine compound represented by formula (B) used in the present invention is a primary or secondary amine compound having the $R^3$ and $R^4$ of the pyrazolecarboxamide derivative represented by formula (C).

$R^3$ and $R^4$ are described in detail. The alkyl group preferably represents a linear or branched alkyl group having 1 to 12 carbon atoms. The alkyl group represented by $R^3$ and that represented by $R^4$ may be bonded to each other to form a ring. The aryl group preferably represents a phenyl or naphthyl group having 6 to 10 carbon atoms. The heterocyclic group preferably represents a 5- to 7-membered, saturated or unsaturated heterocyclic group. These groups may have an organic substituent bonded through a carbon, oxygen, nitrogen, or sulfur atom and a substituent such as a hydroxyl group, a halogen atom, or a sulfo group. Examples of the organic substituent include alkyl groups, aryl groups, heterocyclic groups, a cyano group, acyl groups, a carboxyl group, aryloxy groups, alkoxy groups, heterocycle-oxy groups, an amino group, a sulfamoylamino group, sulfonamido groups, alkylthio groups, arylthio groups, heterocycle-thio groups, a sulfamoyl group, a sulfonyl group, and a sulfinyl group.

The substituents represented by $R^3$ and $R^4$ are explained in more detail.

Examples of the substituted or unsubstituted alkyl group represented by $R^3$ or $R^4$ include methyl, ethyl, propyl, isopropyl, n-butyl, s-butyl, cyclopentyl, cyclohexyl, methoxyethyl, 2-hydroxyethyl, carboxymethyl, phenoxyethyl, methanesulfonylethyl, (3-pentadecylphenoxy)propyl, 3-(2,4diaminophenoxy)propyl, 2-sulfoethyl, 4-sulfobutyl, and 2'-sulfobenzyl.

In the case where the alkyl group represented by $R^3$ is bonded to that represented by $R^4$ to form a ring, this ring is a 5- or 6-membered ring. Examples thereof include pyrrolidino, piperidino, 4-methylpiperazino, 4-ethylpiperazino, and morpholino.

Examples of the substituted or unsubstituted aryl group represented by $R^3$ or $R^4$ include phenyl, 4-tolyl, 4-methoxyphenyl, 2,4-xylyl, 2-chlorophenyl, 4-carboxyphenyl, 4-sulfophenyl, 2,5-disulfophenyl, 1-naphthyl, and 1-(3,5-disulfonaphthyl).

Examples of the substituted or unsubstituted heterocyclic group represented by $R^3$ or $R^4$ include 2-tetrahydrofuranyl, 2-tetrahydrothienyl, 2-pyridyl, 2-thienyl, 2-pyrimidinyl, 2-benzothiazolyl, and 3-(1,1-dioxotetrahydrothienyl).

The substituted or unsubstituted alkyl group represented by $R^3$ or $R^4$ is preferably a substituted or unsubstituted alkyl group having 1 to 7 carbon atoms, and is preferably an unsubstituted methyl group or an alkyl group having 1 to 7 carbon atoms and substituted with a carboxyl, sulfo, alkoxy, or hydroxyl group.

The ring formed when the alkyl group represented by $R^3$ is bonded to that represented by $R^4$ is preferably pyrrolidino, piperidino, 4-methylpiperazino, or morpholino, and is more preferably morpholino.

The substituted or unsubstituted aryl group represented by $R^3$ or $R^4$ is preferably a substituted or unsubstituted phenyl group, and is more preferably an unsubstituted phenyl group or a phenyl group substituted with a carboxyl or sulfo group.

$R^3$ and $R^4$ each preferably represents a hydrogen atom (provided that at least either of $R^3$ and $R^4$ is not a hydrogen atom), an alkyl group having 1 to 7 carbon atoms optionally substituted with a carboxyl, sulfo, alkoxy, or hydroxyl group, or a phenyl group optionally substituted with a carboxyl or sulfo group, or $R^3$ and $R^4$ are preferably bonded to each other to form a morpholino group. More preferably, $R^3$ and $R^4$ each represents a hydrogen atom (provided that at least either of $R^3$ and $R^4$ is not a hydrogen atom), methyl, carboxyethyl, a sulfo-substituted linear alkyl group having 2 to 4 carbon atoms, phenyl, 4-sulfophenyl, or 2,5-disulfophenyl, or $R^3$ and $R^4$ are bonded to each other to form a morpholino group. Particularly preferred are the case where $R^3$ is a hydrogen atom and $R^4$ is phenyl and the case where $R^3$ and $R^4$ are bonded to each other to form a morpholino group, with the latter case being the most preferred.

Specific examples of the amine compound for use in this invention include methylamine, ethylamine, propylamine, isopropylamine, n-butylamine, s-butylamine, cyclopentylamine, cyclohexylamine, methoxyethylamine, 2-hydroxyethylamine, glycine, phenoxyethylamine, methanesulfonylethylamine, (3-pentadecylphenoxy)propylamine, 3-(2,4-diamylphenoxy)-propylamine, 2-sulfoethylamine, 4-sulfobutylamine, 2'-sulfobenzylamine, dimethylamine, diethylamine, dipropylamine, di-n-butylamine, di(methoxyethyl)amine, di(2-hydroxyethyl)amine, pyrrolidine, piperidine, 4-methylpiperazine, 4-ethylpiperazine, morpholine, aniline, 4-toluidine, 4-anisidine, 2,4-dimethylaniline, 2-chloroaniline, 4-aminobenzoic acid, 4-aminobenzenesulfonic acid, 2-aminobenzene-1,4-disulfonic acid, 1-naphthylamine, 1-aminonaphthalene-3,5-disulfonic acid, 2-tetrahydrofuranylamine, 2-tetrahydrothienylamine, 2-pyridylamine, 2-thienylamine, 2-pyrimidinylamine, 2-benzothiazolylamine, and 3-(1,1-dioxotetrahydrothienyl)amine.

In the present invention, the amine compound is preferably used in an amount of from 1 to 10 equivalents to the pyrazolecarboxylic ester compound. The amount thereof is more preferably from 2 to 7 equivalents.

The pyrazolecarboxamide derivative represented by formula (C) is then explained in detail.

$R^1$ has the same meaning as the $R^1$ in formula (A). $R^3$ and $R^4$ have the same meanings as the $R^3$ and $R^4$ in formula (B).

Specific examples of the pyrazolecarboxamide derivative represented by formula (C) synthesized in the present invention are given below, but the pyrazolecarboxamide derivative should not, of course, be construed as being limited thereto.

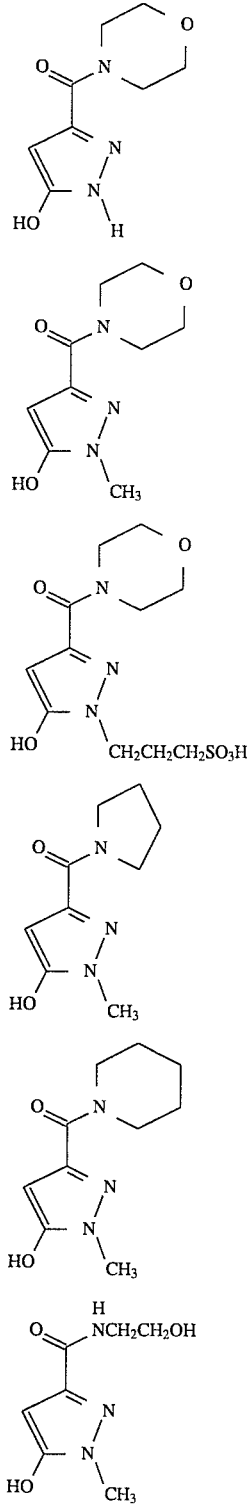

C-1

C-2

C-3

A-4

C-5

C-6

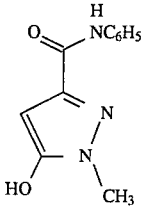

C-7

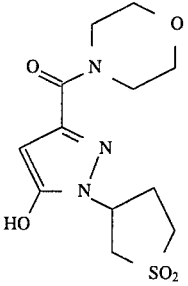

C-8

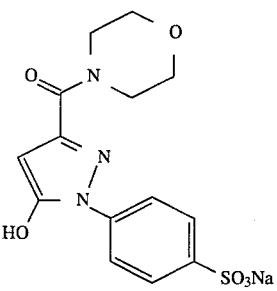

C-9

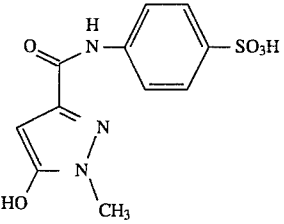

C-10

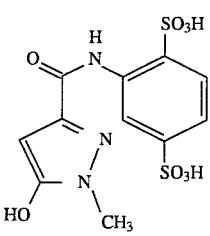

C-11

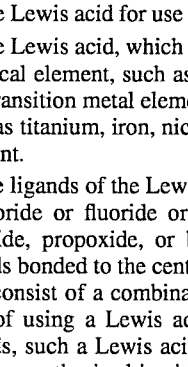

The Lewis acid for use in this invention is then explained.

The Lewis acid, which serves as an electron acceptor, has a typical element, such as boron, aluminum, silicon, or tin, or a transition metal element belonging to the fourth period, such as titanium, iron, nickel, copper, or zinc, as the central element.

The ligands of the Lewis acid are ions of a halide such as a chloride or fluoride or ions of an alkoxide such as an ethoxide, propoxide, or butoxide. In the Lewis acid, the ligands bonded to the central element may be of one kind or may consist of a combination of two or more kinds. In the case of using a Lewis acid having two or more kinds of ligands, such a Lewis acid may be prepared beforehand or may be synthesized in situ through exchange reaction by a well known method (see Kaoru Fuji and Manabu Noide,

*Yuki Gōsei Kagaku* (Organic Synthesis Chemistry), 42, 194 (1984)).

Specific examples of the Lewis acid for use in this invention include boron trihalides such as boron trifluoride, boron trichloride, and boron tribromide, aluminum trihalides such as aluminum chloride and aluminum bromide, tin tetrahalides such as tin tetrachloride, tin dihalides such as tin dichloride, titanium tetrahalides such as titanium tetrachloride, titanium trihalides such as titanium trichloride, titanium alkoxides such as titanium isopropoxide, iron dihalides such as iron dichloride, iron trihalides such as iron trichloride, nickel dihalides such as nickel dichloride, and zinc halides such as zinc chloride and zinc bromide.

More preferred Lewis acids are boron trihalides, aluminum trihalides, tin tetrahalides, titanium tetrahalides, titanium alkoxides, iron trihalides, and zinc halides. Further preferred of these are iron trichloride, aluminum chloride, titanium isopropoxide, titanium tetrachloride, and zinc chloride, with aluminum chloride being the most preferred.

In the present invention, the Lewis acid may be used in any desired amount in the range of from 0.0005 to 1 equivalent to the amine compound. It is particularly preferred to use the Lewis acid as a catalyst. In this case, the amount thereof is preferably from 0.0005 to 0.35 equivalent, most preferably from 0.005 to 0.2 equivalent.

Various solvents may be used in carrying out the reaction of the present invention. Examples of usable solvents include aromatic hydrocarbons such as toluene and xylene, halogenated hydrocarbons such as chloroform, chlorobenzene, and o-dichlorobenzene, ethers such as tetrahydrofuran and dimethoxyethane, dimethyl sulfoxide, and sulfolane. It is possible to use the amine compound in excess so as to utilize it also as a solvent.

Preferred solvents are toluene, xylene, cumene, chlorobenzene, o-dichlorobenzene, dimethoxyethane, sulfolane, and an excess amine. More preferred of these are toluene, xylene, chlorobenzene, and an excess amine, with an excess amine being the most preferred.

The reaction temperature is from 0° to 200° C., preferably from 20° to 150° C. In the case of reaction with morpholine, the reaction temperature is more preferably from 80° to 130° C.

The reaction is preferably carried out in a nitrogen atmosphere in order to prevent oxidation of the reaction product.

In a preferred embodiment of the present invention, in formulae (A) to (C), $R^1$ is a hydrogen atom, an alkyl group having 1 to 7 carbon atoms optionally substituted with a carboxyl, sulfo, or hydroxyl group, a phenyl group optionally substituted with a carboxyl or sulfo group, or 3-(1,1-dioxotetrahydrothienyl); $R^2$ represents an alkyl group having 1 to 6 carbon atoms; and $R^3$ and $R^4$ each represents a hydrogen atom (provided that at least either of $R^3$ and $R^4$ is not a hydrogen atom), an alkyl group having 1 to 7 carbon atoms optionally substituted with a carboxyl, sulfo, alkoxy, or hydroxyl group, or a phenyl group optionally substituted with a carboxyl or sulfo group, or $R^3$ and $R^4$ are bonded to each other to form a morpholino group. In this preferred embodiment, a Lewis acid selected from boron trihalides, aluminum trihalides, tin tetrahalides, titanium tetrahalides, titanium alkoxides, iron trihalides, and zinc halides is used as a catalyst in an amount of from 0.0005 to 0.35 equivalent.

The present invention will be explained below in more detail by reference to Examples.

EXAMPLE 1

Synthesis of 3-Ethoxycarbonyl-5-hydroxypyrazole

To 400 ml of ethanol were added 20.6 g (0.30 mol) of the hydrazine hydrochloride and 63.0 g (0.30 mol) of sodium diethyloxalacetate. This mixture was stirred at room temperature for 2 hours, and then heated with refluxing and stirring for 3 hours. After the ethanol was distilled off, 100 ml of water was added to the residue. The resulting mixture was stirred at room temperature for 1 hour, and the crystals yielded were taken out by filtration and washed with water.

Yield: 30.2 g (65%). Melting point: 180°–182° C.

Synthesis of Compound C-1

A mixture of 15.6 g (0.10 mol) of 3-ethoxycarbonyl-5hydroxypyrazole, 35 ml (0.40 mol) of morpholine, and 1.33 g (0.01 mol) of anhydrous aluminum chloride was stirred at 100° C. in a nitrogen atmosphere for 7 hours. After the excess morpholine was distilled off under reduced pressure, 30 ml of saturated aqueous common salt solution was added to the residue. The pH of the resulting mixture was adjusted to 4 with concentrated hydrochloric acid, and the crystals yielded were taken out by filtration and washed with saturated aqueous common salt solution. Yield: 16.2 g (83%). Melting point*: 220° C.-decomposition.

(*: The crystals were changed to brown color at a temperature of at least 220° C. without showing a clear melting point.)

EXAMPLE 2

Synthesis of 3-Ethoxycarbonyl-5-hydroxy-1-methylpyrazole

To 800 ml of ethanol were added 108 g (1.1 mol) of sulfuric acid, 92.1 g (2.0 mol) of methylhydrazine, and 462.4 g (2.20 mol) of sodium diethyloxalacetate. This mixture was stirred at room temperature for 2 hours, and then heated with refluxing and stirring for 3 hours. After the ethanol was distilled off, 800 ml of water was added to the residue. The resulting mixture was allowed to stand at room temperature overnight, and the crystals yielded were taken out by filtration and washed with water. Yield: 279 g (82%). Melting point: 151°–153° C.

Synthesis of Compound C-2

A mixture of 17.0 g (0.10 mol) of 3-ethoxycarbonyl-5-hydroxy-1-methylpyrazole, 35 ml (0.40 mol) of morpholine, and 1.33 g (0.01 mol) of anhydrous aluminum chloride was stirred at 110° C. in a nitrogen atmosphere for 5 hours. After the excess morpholine was distilled off under reduced pressure, 35 ml of saturated aqueous common salt solution was added to the residue. The pH of the resulting mixture was adjusted to 4 with concentrated hydrochloric acid, and the crystals yielded were taken out by filtration and washed with saturated aqueous common salt solution. Yield: 18.2 g (86%). Melting point: 172°–174° C.

EXAMPLE 3

Synthesis of Compound C-2

A mixture of 17.0 g (0.10 mol) of 3-ethoxycarbonyl-5-hydroxy-1-methylpyrazole, 35 ml (0.40 mol) of morpholine, and 5.69 g (0.02 mol) of titanium isopropoxide was stirred at 110° C. in a nitrogen atmosphere for 7 hours. After the excess morpholine was distilled off under reduced pressure, 35 ml of saturated aqueous common salt solution was added to the residue. The pH of the resulting mixture was adjusted to 4 with concentrated hydrochloric acid, and the crystals yielded were taken out by filtration and washed with saturated aqueous common salt solution. Yield: 17.3 g (82%).

EXAMPLE 4

Synthesis of Compound C-2

A mixture of 17.0 g (0.10 mol) of 3-ethoxycarbonyl-5-hydroxy-1-methylpyrazole, 35 ml (0.40 mol) of morpholine, and 3.24 g (0.02 mol) of anhydrous iron trichloride was stirred at 110° C. in a nitrogen atmosphere for 5 hours. After the excess morpholine was distilled off under reduced pressure, 35 ml of saturated aqueous common salt solution was added to the residue. The pH of the resulting mixture was adjusted to 4 with concentrated hydrochloric acid, and the crystals yielded were taken out by filtration and washed with saturated aqueous common salt solution. Yield: 18.0 g (85%).

EXAMPLE 5

Synthesis of Compound C-2

A mixture of 17.0 g (0.10 mol) of 3-ethoxycarbonyl-5-hydroxy-1-methylpyrazole, 35 ml (0.40 mol) of morpholine, and 1.36 g (0.01 mol) of anhydrous zinc chloride was stirred at 110° C. in a nitrogen atmosphere for 5 hours. After the excess morpholine was distilled off under reduced pressure, 35 ml of saturated aqueous common salt solution was added to the residue. The pH of the resulting mixture was adjusted to 4 with concentrated hydrochloric acid, and the crystals yielded were taken out by filtration and washed with saturated aqueous common salt solution. Yield: 18.4 g (87%).

EXAMPLE 6

Synthesis of 3-(3-Ethoxycarbonyl-5-hydroxypyrazol)-1-yl-propanesulfonic acid A mixture of 31.4 g (0.2 mol) of 3-ethoxycarbonyl-5-hydroxypyrazole, 24.4 g (0.2 mol) of purified propanesultone, and 100 ml of xylene was stirred with heating at 150° C. for 2 hours. After the reaction mixture was allowed to separate into two layers, the supernatant was removed by decantation. To the residual sticky oil was added 50 ml of methanol. The resulting mixture was stirred with heating to be dissolved, and then cooled with ice. At the time when crystals began to precipitate, 40 ml of acetone was added. This mixture was maintained at 5° C. or lower overnight in a refrigerator, and the crystals thus precipitated were taken out by filtration. Yield: 23.3 g (42%). Melting point: 107°–109° C.

Synthesis of Compound C-3

A mixture of 11.1 g (0.04 mol) of 3-(3-ethoxy-carbonyl-5-hydroxypyrazol)-1-ylpropanesulfonic acid, 28 ml (0.32 mol) of morpholine, and 0.53 g (0.004 mol) of anhydrous aluminum chloride was stirred at 110° C. in a nitrogen atmosphere for 5 hours. After the excess morpholine was distilled off under reduced pressure, 10 ml of saturated aqueous common salt solution was added, following which 10 ml of concentrated hydrochloric acid was added with cooling with ice. The resulting mixture was maintained at 5° C. or lower for 24 hours. The crystals thus precipitated were taken out by filtration. The yield was 12.1 g. Although this reaction product contained about 20% common salt as an impurity, it was usable as a dye intermediate without further purification.

EXAMPLE 7

3-Ethoxycarbonyl-5-hydroxy-1-sulfolanylpyrazole was synthesized in the same manner as in Example 1. The sulfolanylhydrazine used as a starting compound was synthesized according to *Annalender Chemie,* 681, 105 (1965).

Synthesis of Compound C-8

A mixture of 11.0 g (0.04 mol) of 3-ethoxycarbonyl-5-hydroxy-1-sulfolanylpyrazole, 35 ml (0.4 mol) of morpholine, and 0.53 g (0.004 mol) of anhydrous aluminum chloride was stirred at 110° C. in a nitrogen atmosphere for 5 hours. After the excess morpholine was distilled off under reduced pressure, 20 ml of saturated aqueous common salt solution was added to the residue. The pH of the resulting mixture was adjusted to 4 with concentrated hydrochloric acid, and the crystals precipitated were taken out by filtration. Yield: 12.5 g (99%). Melting point: 224°–227° C.

EXAMPLE 8

Synthesis of Compound C-7

A mixture of 1.70 g (0.010 mol) of 3-ethoxycarbonyl-5-hydroxy-1-methylpyrazole, 7.3 ml (0.080 mol) of aniline, and 0.13 g (0.001 mol) of anhydrous aluminum chloride was stirred at 110° C. in a nitrogen atmosphere for 3 hours. After the reaction mixture was cooled to room temperature, the crystals precipitated were taken out by filtration and washed with isopropanol. Yield: 2.38 g (100%). Melting point*: 252° C.-decomposition.

(*: The crystals were changed to brown color at a temperature of at least 252° C. without showing a clear melting point.)

COMPARATIVE EXAMPLE 1

Synthesis of Compound C-2

To 117 ml (1.32 mol) of morpholine was added 56.7 g (0.33 mol) of 3-ethoxycarbonyl-5-hydroxy-1-methylpyrazole. This mixture was stirred at 130° C. in a nitrogen atmosphere for 18 hours, while the ethanol yielded was removed. After the excess morpholine was distilled off under reduced pressure, 100 ml of saturated aqueous common salt solution was added to the residue. The pH of the resulting mixture was adjusted to 4 with concentrated hydrochloric acid, and the crystals yielded were taken out by filtration and washed with saturated aqueous common salt solution. Yield: 58.1 g (82%).

COMPARATIVE EXAMPLE 2

Synthesis of Compound C-3

A mixture of 17.0 g (0.10 mol) of 3-(3-ethoxy-carbonyl-5-hydroxypyrazol)-1-ylpropanesulfonic acid and 35 ml (0.40 mol) of morpholine was stirred at 110° C. in a nitrogen atmosphere for 5 hours. After the excess morpholine was distilled off under reduced pressure, 100 ml of saturated aqueous common salt solution was added to the residue. The pH of the resulting mixture was adjusted to 4 with concentrated hydrochloric acid, and the solid yielded was taken out by filtration and washed with saturated aqueous common salt solution. The yield was 19.9 g. The thus-obtained solid contained the unreacted starting ester in an amount of 47%.

The process of the present invention is advantageous in that not only a relatively low reaction temperature can be used, but the reaction time can be reduced. The process is extensively usable for synthesizing pyrazolecarboxamide derivatives having a carbamoyl group at the 3-position.

While the invention has been described in detail and with reference to specific embodiments thereof, it will be apparent to one skilled in the art that various changes and modifications can be made therein without departing from the spirit and scope thereof.

What is claimed is:

1. A process for producing a pyrazolecarboxamide derivative represented by formula (C) which comprises reacting a pyrazolecarboxylic ester compound represented by formula (A) with an amine compound represented by formula (B) in the presence of a Lewis acid:

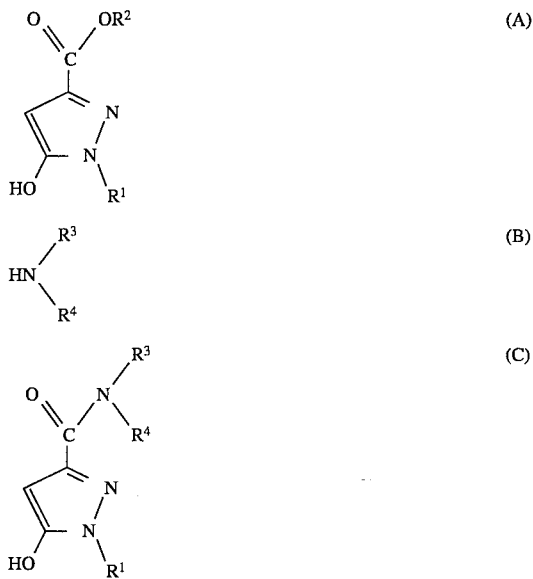

wherein $R^1$ represents a hydrogen atom, a substituted or unsubstituted alkyl group, a substituted or unsubstituted aryl group, or a substituted or unsubstituted heterocyclic group; $R^2$ represents a substituted or unsubstituted alkyl group; and $R^3$ and $R^4$ each represents a hydrogen atom, a substituted or unsubstituted alkyl group, a substituted or unsubstituted aryl group, or a substituted or unsubstituted heterocyclic group, provided that $R^3$ and $R^4$ may be bonded to each other to form a ring.

2. The process for producing a pyrazolecarboxamide derivative as claimed in claim 1, wherein the Lewis acid is used in an amount of from 0.0005 to 0.35 equivalent to the amine compound.

3. The process for producing a pyrazolecarboxamide derivative as claimed in claim 1, wherein the amine compound is a 5- or 6-membered ring which is formed by bonding of the alkyl group represented by $R^3$ to that represented by $R^4$.

4. The process for producing a pyrazolecarboxamide derivative as claimed in claim 3, wherein the 5- or 6-membered ring is selected from the group consisting of pyrrolidino, piperidino, 4-methylpiperazino, 4-ethyl-piperazino and morpholino.

5. The process for producing a pyrazolecarboxamide derivative as claimed in claim 4, wherein the 5- or 6-membered ring is morpholino.

6. The process for producing a pyrazolecarboxamide derivative as claimed in claim 1, wherein the amine compound is used in an amount of from 1 to 10 equivalents to the pyrazolecarboxylic ester compound.

7. The process for producing a pyrazolecarboxamide derivative as claimed in claim 6, wherein the amine compound is used in an amount of from 2 to 7 equivalents to the pyrazolecarboxylic ester compound.

8. The process for producing a pyrazolecarboxamide derivative as claimed in claim 1, wherein the Lewis acid is selected from the group consisting of iron trichloride, aluminum chloride, titanium isopropoxide, titanium tetrachloride and zinc chloride.

9. The process for producing a pyrazolecarboxamide derivative as claimed in claim 8, wherein the Lewis acid is aluminum chloride.

10. The process for producing a pyrazolecarboxamide derivative as claimed in claim 1, wherein the reaction is carried out at a temperature of from 80° to 130° C.

11. The process for producing a pyrazolecarboxamide derivative as claimed in claim 1, wherein the reaction is carried out in the presence of a solvent selected from the group consisting of aromatic hydrocarbons, halogenated hydrocarbons, ethers, dimethyl sulfoxide and sulfolane.

* * * * *